United States Patent [19]

Hutchins

[11] Patent Number: 4,584,865
[45] Date of Patent: Apr. 29, 1986

[54] DEVICE AND METHOD FOR TESTING FOR MOTOR BEARING WEAR

[75] Inventor: Clement Hutchins, Moultonboro, N.H.

[73] Assignee: Lawrence Pump and Engine Company, Lawrence, Mass.

[21] Appl. No.: 635,901

[22] Filed: Jul. 30, 1984

[51] Int. Cl.[4] .............................................. G01N 3/56
[52] U.S. Cl. ...................................... 73/7; 324/65 R; 340/682
[58] Field of Search ................... 73/7; 324/454, 65 R; 340/682

[56] References Cited

U.S. PATENT DOCUMENTS

| | | | |
|---|---|---|---|
| 1,996,063 | 4/1935 | Corkran | 324/65 R |
| 2,805,663 | 10/1957 | Hornbostel | 340/682 X |
| 2,981,929 | 4/1961 | Rizzo et al. | 73/7 X |
| 3,108,264 | 10/1963 | Heinoo | 340/682 |
| 3,508,241 | 4/1970 | Potter | 340/682 |
| 3,775,680 | 11/1973 | Egeland | 73/7 X |
| 3,958,445 | 5/1976 | Howard et al. | 73/7 |
| 3,991,701 | 11/1976 | Sato | 116/208 |
| 4,095,552 | 6/1978 | Lo | 73/7 X |
| 4,140,015 | 2/1979 | Roley | 340/682 X |
| 4,320,431 | 3/1982 | Bell | 340/682 X |

FOREIGN PATENT DOCUMENTS

| | | | |
|---|---|---|---|
| 296707 | 6/1914 | Fed. Rep. of Germany | 340/682 |
| 1559959 | 1/1980 | United Kingdom | 73/7 |
| 727886 | 4/1980 | U.S.S.R. | 340/682 |
| 991256 | 1/1983 | U.S.S.R. | 73/7 |

OTHER PUBLICATIONS

"Electrochemical Evaluation of the Wear Resistance of Steel and Cast Iron", *Sov. Mater. Sci. (USA)*; vol. 14, No. 2, Nov. 1978, pp. 159-162, Yu. I. Babel et al.
"Accelerated Wear Testing of PTFE Composite Bearing Materials", *Tribiology International*, vol. 12, No. 2, pp. 65-75, Apr. 1979, J. K. Lancaster.

*Primary Examiner*—Stewart J. Levy
*Assistant Examiner*—Tom Noland
*Attorney, Agent, or Firm*—Pearson & Pearson

[57] ABSTRACT

A canned motor pump has a bearing wear sensing device comprising a pair of ring elements having opposing surfaces. The outer element is mounted fixed with respect to the stator and the inner element is mounted for rotation with the rotor. The outer, fixed element is coated with polytetrafluoroethylene. An ohmmeter measures the resistance between the elements through the coating. As the motor bearings wear, displacement of the rotating element causes wear of the coating which reduces its thickness and decreases the resistance between the sensing elements through the coating. One conductor of the ohmmeter is connected directly to the outer, fixed element, and the other ohmmeter conductor is connected through the conductive bearings to the rotating element. Thus, the ohmmeter can dynamically measure the motor bearing wear.

11 Claims, 4 Drawing Figures

DEVICE AND METHOD FOR TESTING FOR MOTOR BEARING WEAR

FIELD OF THE INVENTION

The invention relates to canned motors, and more particularly to a device and method for testing for the bearing wear in a canned motor.

BACKGROUND OF THE INVENTION

The detection and testing for bearing wear is of importance, especially for canned pumps. Bearing wear may cause serious and expensive damage to the cans which contain the canned pumps, or to the pumps. Therefore, it is important to detect bearing wear before some catastrophic damage to the pump or motor occurs. Bearing wear detection devices and methods for this purpose are known. For example:

U.S. Pat. No. 1,788,941 to Bradley, et al, June 23, 1927, for Device For Indicating Undue Wear In Bearings employs a probe adjacent the connecting rod of an internal combustion engine. When the crankshaft bearing wears unduly, the resultant crankshaft departure from its usual motion is imparted to the probe, from which an indication of the excessive wear may be taken.

U.S. Pat. No. 3,542,494 to Sato Nov. 24, 1970, for Canned Motor Pump describes a bearing checking device in which a tube filled with inert gas under pressure is ruptured by a rotary shaft portion when bearing wear exceeds certain limits. The reduction in pressure in the tube is detected to indicate the excessive bearing wear.

U.S. Pat. No. 3,991,701 to Sato, Nov. 16, 1976, for Bearing Wear Detecting Device For Canned Motor Driven Pumps describes a chamber on the rotor which rotates about a fixed tube containing gas under pressure. Bearing wear causes the chamber to wear against the tube, rupturing the tube, which results in reduced gas pressure indicating the excessive bearing wear.

U.S. Pat. No. 4,095,552 to Lo, June 20, 1978, for Dummy Bearing For Bearing Wear Detection employs a dummy bearing structured to wear like the main bearing, either for thrust or radially, and the dummy bearing is directly inspected for excessive wear.

U.S. Pat. No. 4,175,331 to Johnson for Shaft Bearing Wear Measuring Apparatus Nov. 27, 1979, uses a probe attached to a transducer. When the probe is urged against the rotor shaft, a voltage may be detected by the transducer which indicates bearing wear.

U.S. Pat. No. 4,199,718 to Ikeda, et al, Apr. 22, 1980 for Bearing Wear Detector For AC Rotary Electric Instrument, suggests using three series connected coils spaced around poles driven by the rotor. Analysis of the voltage waves induced in the coils affords an indication of the bearing wear.

U.S. Pat. No. 4,320,431 to Bell, Mar. 16, 1982 for Fluid Circulating Pump describes a motor pump, suggests employing non-conductive bearings and conductive detecting rings held by the bearings disposed to be contacted by the motor shaft when bearing wear occurs. When the contact rings come into contact with the rotor, a circuit is completed indicating the wear and by setting off an alarm or halting operation of the motor.

Other patents generally related to bearing wear, for example, are:

U.S. Pat. No. 3,572,976 to Sato, Mar. 30, 1971 for Fluid Take-Off Device For Canned Motor Driven Pump, rotates a portion of the pumped fluid to the rotor in a fashion to reduce thrust bearing wear.

U.S. Pat. No. 3,637,329 to Sato, et al, Jan. 25, 1972, for Pump, describes a canned motor pump with means for using the pumped fluid to balance rotor thrust.

SUMMARY OF THE INVENTION

According to the invention, in a motor having a stator and rotor, a conductive ring element is fixed with respect to the stator coaxially with the rotor, and another conductive element is attached coaxially to and supported for rotation by the rotor. The ring elements have opposed surfaces, one of which is coated with a non-conductive coating, preferably polytetrafluoroethylene. Means are provided for measuring the resistance between the ring elements through the non-conductive coating, said means being connected through an electrical path including the bearings to the respective elements.

BRIEF DESCRIPTION OF THE DRAWINGS

The various objects, advantages, and novel features of the invention will be more fully apparent from the following detailed description when read in connection with the accompanying drawings, in which like reference numerals refer to like parts, and in which:

FIG. 1, comprising

DESCRIPTION OF THE DRAWINGS

Figure 1A:
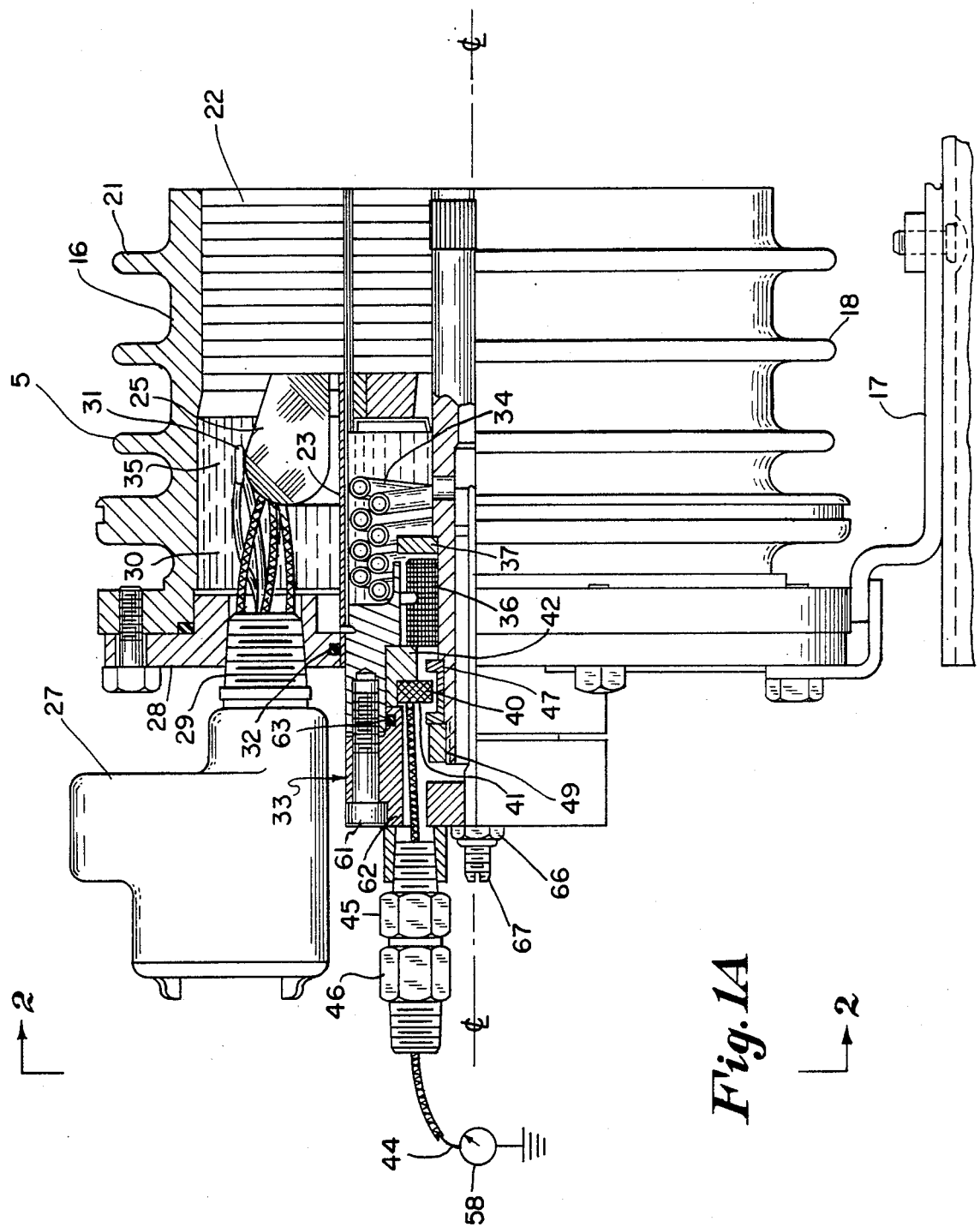
FIGS. 1A and 1B is a longitudinal view, partly in section, of a canned motor embodying the invention.
Figure 1B:
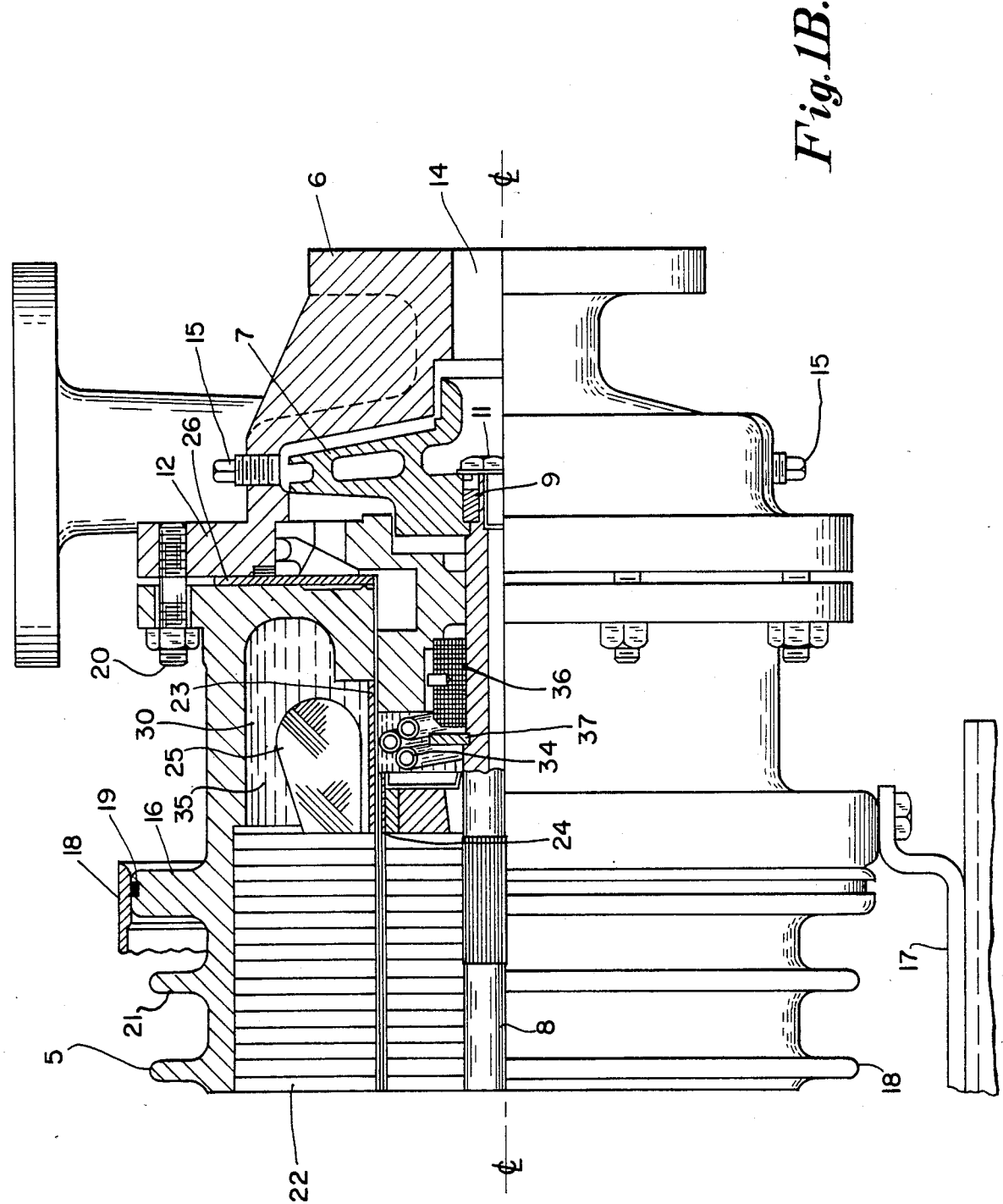

A canned motor 5, actuates a pump 6. The pump includes impeller 7, mounted on the motor rotor 8, and keyed thereto by key 9. A bolt 11 holds the impeller fast to the rotor 8. An impeller and pump housing 12 serves also as a right (as viewed in FIG. 1) end plate for the motor 5. The pump housing 12, has an internally voluted chamber accommodating the impeller 7, and leading to the pump exit, the entrance being at a central aperture 14. The rotor 8 and impeller 7, rotate about an axis which is the indicated line of the drawing indicated by the conventional symbol ¢. Only a portion above the center line is detailed in cross section in FIG. 1. Vent and drain plugs 15 are provided.

The canned motor 5 has a housing 16, suitably supported on a base 17, fastened to the housing with bolts or the like. A water cooling jacket 18 is sealed to the housing 16, by O-rings 19, and housing vanes 21, assist in rapid heat transfer. The motor stator 22, is canned or enclosed by a thin, non-magnetic metallic can 23, the rotor is sealed by a thin, non-magnetic metallic can 24. The pump housing 12 is fastened to the motor housing 16, by studs 20, and the two housings are sealed together by a gasket 26.

Windings 25, for stator 22, are brought in through a conduit 27, fitted through an end plate 28, by a suitable threaded nipple 29, into a cavity 30, which may carry oil 35, or the like. The leads to a thermo-couple 31, also pass through conduit 27. The thermocouple 31 is placed adjacent stator winding 25, to sense a too high temperature which would indicate excess motor currents. The end plate 28, closes the left end (as viewed in FIG. 1) of the motor housing 16. The housing 16, is sealed to its end plate 28, by an O-ring 32, about cup portion 33. Cooling coils 34 may be disposed in a cavity in the motor housing 16 to cool rotor bearings 36, and thrust bearings or retaining rings 37. The bearings, especially rotor bearings 36 are of any suitable conductive material, preferably carbon, and should of course, afford a low frictional engagement against the rotation of rotor 8, at the same time making with rotor 8 a good electrical contact.

In order to provide an indication of bearing wear, an outer ring 41 (a ring element) coated with a coating 40, is disposed in the stator cup portion 33 supported in a fixed retainer 42.

Figure 2:
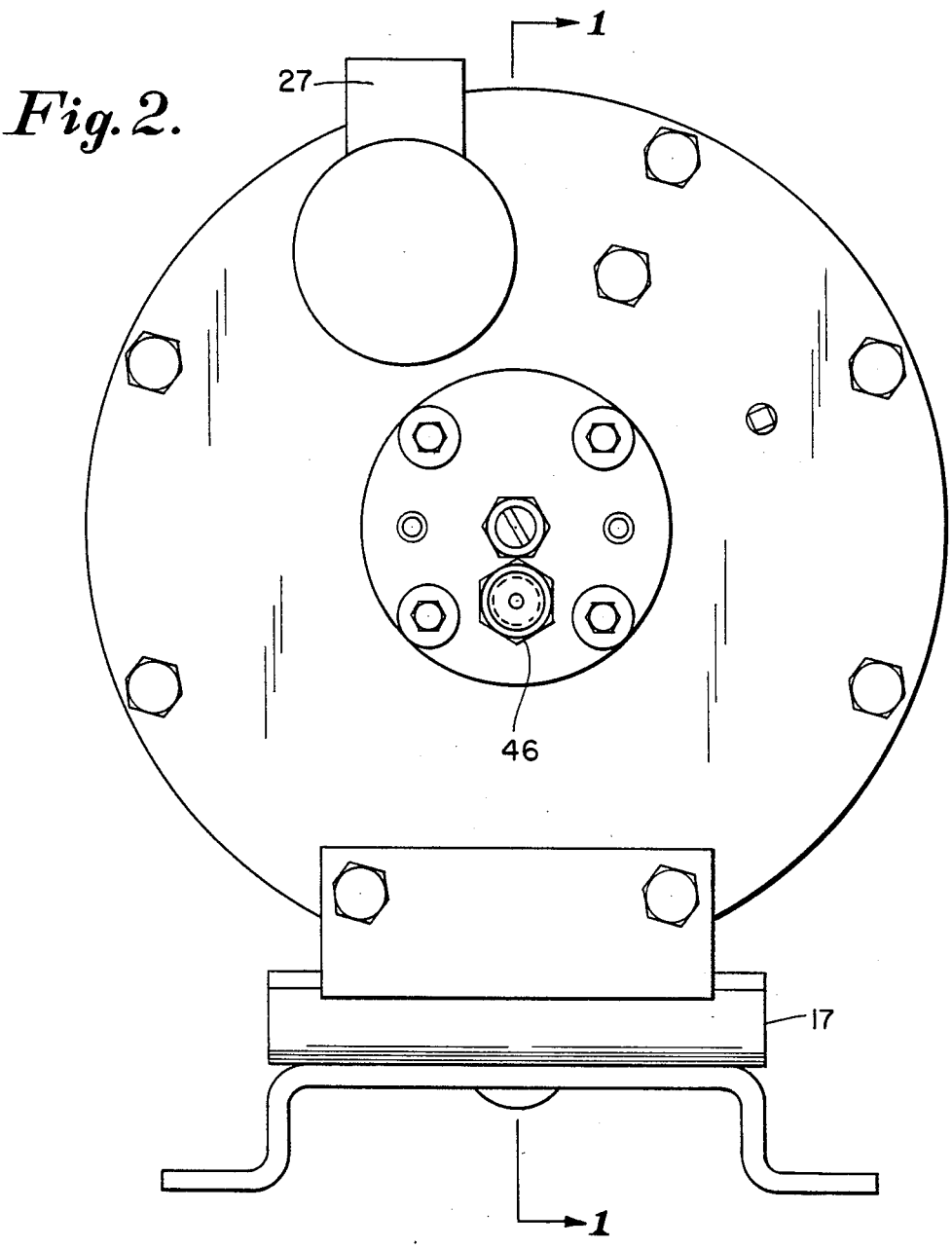
FIG. 2, is an end view of the motor of FIG. 1.
Figure 3:
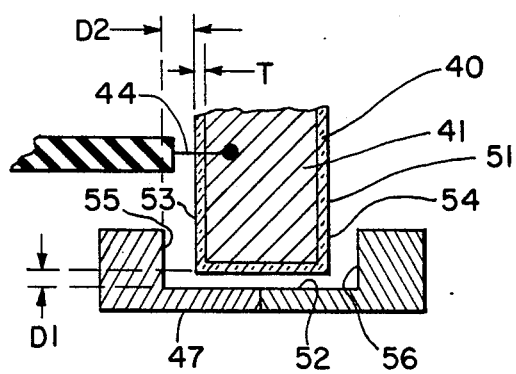
FIG. 3 is a partial cross-sectional view of the ring elements of FIG. 1.

An insulated conductor 44, connected to the ring 41, passes inside a feed through gland 46. Note that gland 46 is shown for ease in drafting in FIG. 1, displaced 180° from its true position shown in FIG. 2. The outer ring coating 40 is of polytetrafluoroethylene, which has high resistivity, and is very hard. The coating is very thin to afford a measurable resistivity, a thickness T(FIG. 3) of, say, 0.006 inch. The entire ring may be coated for convenience. Further to provide an indication of bearing wear, there is provided an inner ring 47 (a ring element) fitted into a complementary outer cylindrical surface of the rotor 8 and held in place by a nut 49 threaded onto the shaft. The adjacent outer and inner rings 41 and 47, have opposed faces shown in a larger partial view in FIG. 3. The outer ring 41, inner face 51, and the inner ring 47, outer face 52, face each other. The inner ring element outer face 51 has also axial surface components at 53 and 54, and inner ring element 47 has axial surface components at 55 and 56 which face the respective axial components of the outer surface of ring element 41. The radially extending facing components will wear as a result of axial bearing wear, i.e. thrust bearing wear, and the axially extending facing components will wear against each other as a result of wear in the radial bearings 36. The outer ring element coating 40 of polytetrafluoroethylene may be Teflon (a trademark of the DuPont Company). An ohmmeter 58 is connected to the outer ring element 41 by the conductor 44. The other electrical terminal of ohmmeter 58 is connected to what is indicated as a common ground by the conventional symbol, which may be connected to the motor housing 16, and through the housing and through the conductive bearings 36, to the inner rotor element 47. Bolts 61 engaged in the motor housing 16 hold against the housing 16 a box 62, for the gland 45. The box 62 is sealed to the housing by an O-ring 63 leaving a passageway for the wire 44, which has a suitable insulative covering.

A center thrust assembly is affixed to the housing with a nut 66 through which an adjustment screw 67 provides for adjusting.

In operation, when the motor is rotating, should there be bearing water, opposed surfaces of the rings 41 and 47 will come into contact causing wear on the coating 40. As the resistance between elements 41 and 47 through the coating 40 decreases as a result of the wear, the resistance measured by the ohmmeter 44 decreases, and the decreased resistance observed. Such a decrease in resistance indicates, and is a measure, of bearing wear. Thus, the bearing wear may be estimated or measured dynamically, that is, during rotor and pump rotation, without operation interruption. A critical resistance reading would indicate wear that would lead to a failure of the bearings, or perhaps to a catastrophic failure. As understood in the art, knowledge of a possible failure due to bearing wear is of great importance, especially in canned motor pumps. Dynamic indication is of special importance and value in cases in which the pumps are used in long term, continuous usage to pump noxious or toxic materials. Of course, the resistance calling for stoppage may be monitored automatically, so that if the resistance falls to such a value, an alarm may ring, or the operation may be automatically halted, by connecting suitable equipment to the ohmmeter.

In one embodiment in which the rotor diameter was about 3.049 inches, the polytetrafluoroethylene coating 40 had a thickness of about 0.006 inch, the nominal initial separation, or radial clearance, D1 of the surfaces 51 and 52 was about 0.005 inch, and the nominal initial axial clearance or separation D2 of the surfaces 53 and 55 (the same as between the surfaces 54 and 56) was about 3/16 of an inch. The resistance measure may extend from about $3 \times 10^5$ ohms initially, and a bearing wear calling for inspection or replacement or the like, may be of below $3 \times 10^3$ ohms.

As mentioned above, the means and method described using resistance measurements is of particular and special value in the operation of canned motor rotor pumps. In many applications of these pumps wear on the bearings may cause catastrophic effects on the cans and the motor, or destroy the seals which contain the pumped fluid. Such fluids are sometimes noxious, or even toxic. The escape of these fluids is, therefore, dangerous. Thus, the invention is of particular importance in use with canned motor pumps.

"Teflon" is preferred as the coating because it is compatible with most industrial fluids to be pumped. Except for this, any other impervious insulation would suffice. Vinyl insulations would be suitable for some applications, but do not have lower temperature limits and are not compatible with many industrial chemicals. The entire ring must be coated to insure insulation when conductive fluids are being pumped.

The above mentioned Bell Patent, U.S. Pat. No. 4,320,431 is for dielectric fluids only while the pump of this invention is not dependent on the fluid for electric insulation.

I claim:

1. In a motor having a stator, means for supporting conductive bearings fixed with respect to the stator, and a rotor supported by the bearings for rotation about an axis, a device for testing for bearing wear comprising:
   a conductive ring element fixed with respect to the stator and co-axial with the rotor axis;
   a conductive rotary ring element co-axial with and attached to and supported for rotation with the rotor;
   one of the ring elements having an internal surface and the other ring element having an external surface, the internal and external surfaces facing each other closely, one of said facing surfaces being coated with a resistive coating; and
   means for dynamically measuring the resistance between the ring elements through the resistive coating, said means being connected between the fixed element through an electrical path including the bearings to the rotary element;
   whereby wear of the bearings causes wear of the coating and the resistance measuring means dynamically indicates a decreased resistance between the rings through the coating as a measure of the degree of bearing wear.

2. A device as claimed in claim 1, said fixed ring element being insulated except for its electrical connection to the resistance measuring means, and said rotary element being electrically connected through the bearings to the resistance measuring means.

3. A device as claimed in claim 1, said motor comprising a housing having an end plate, said fixed ring element being held in and insulated from the housing end plate, said bearings being held in and in electrical contact with said housing.

4. A device as claimed in claim 3, the one coated surface being a surface of said fixed ring element, and the coating being of tetrafluoroethylene.

5. A device as claimed in claim 3, said facing surfaces having both radial and axial components, the one coated surface being a surface of the fixed element, the coating of the coated surface being of tetrafluoroethylene.

6. A device as claimed in claim 1, the coated one of said facing surfaces being coated with tetrafluoroethylene.

7. A device as claimed in claim 1, said facing surfaces including both axial and radial surface components.

8. A device as claimed in claim 7, the one coated surface being a surface of said fixed ring element, and the coating being of tetrafluoroethylene.

9. A method of dynamically testing for bearing wear in a canned motor having a rotor, a stator and electrically conductive bearings for the rotor and stator, comprising the steps of:
providing a conductive element having an insulating coating and fixed with respect to the motor stator;
providing a rotary element carried by the motor rotor and subject to motion relative to the stator element as the bearings are subjected to wear;
said rotary element wearing against the insulative coating to reduce the thickness of the coating; and
dynamically measuring through an electrical path including the bearings the reduced resistance between the elements due to reduced thickness with wear of the coating to indicate dynamically the degree of bearing wear.

10. A method as claimed in claim 9, said elements having the opposed surfaces of both radial and of axial extent, whereby bearing wear producing axial or radial rotor displacement with wear is indicated.

11. A method as claimed in claim 9:
said measuring of resistance being performed as the motor rotor is rotating with the motor in operation.

* * * * *